United States Patent [19]

Hope

[11] Patent Number: Plant 5,594

[45] Date of Patent: Dec. 10, 1985

[54] IMPATIENS PLANT NAMED VISTA IMPATIENS NO. 10

[75] Inventor: Claude Hope, Cartago, Costa Rica

[73] Assignee: Pan American Plant Company, Parrish, Fla.

[21] Appl. No.: 566,805

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant named Vista Impatiens No. 10 characterized by its vivid red and large flowers, dark green foliage, profuse blooming, and tall and upright habit, making it suitable for bedding plants and pot plant culture.

1 Drawing Figure

The present invention relates to a new and distinctive cultivar of impatiens plant, botanically known as Impatiens, and known by the cultivar name Vista Impatiens No. 10.

The new cultivar is the result of a planned program of hybridization the purpose of which was to obtain a series of plants having a wide range of colors and with very large flowers derived from the New Guinea complex of species collected by the Longwood Garden Expedition of 1970. The new cultivar was selected in 1981 and designated seedling No. 3096-63-1. The cultivar was produced from a cross of seedling No. 3063-3-3 × seedling No. 3096-1.

Asexual reproduction by terminal or stem cuttings taken by me at Cartago, Costa Rica has shown that the unique features of this new impatiens are stabilized and are reproduced true to type in successive propagations.

The following characteristics distinguish the new impatiens from both its parent varieties and other cultivated impatiens of this type known and used in the floriculture industry.

1. Vista Impatiens No. 10 was selected and is principally characterized by its vivid coloring, profuse flowering, superior self-branching, and tall and upright habit.

2. Flowers are a vivid red in color, profuse and large (60 mm.). The flowers appear early in plant development and bloom throughout the growing season.

3. Foliage color is dark green, providing a strking contrast with the flowers.

4. Habit is tall and upright (45–60 cm.), making it suitable for bedding plants and pot plant culture.

5. . The branching is excellent and upright.

6. Good keeping qualities when grown outside in full sun (fall, winter and spring) or under light shade (summer) in Florida.

7. Growth rate is moderate, producing in 6–8 when grown outside a saleable plant 20–30 cm. tall and 20–25 cm. in diameter, in a 5½" pot.

The accompanying colored photograph illustrates the overall appearance of this cultivar, showing the colors as true as it is reasonably possible to obtain in a colored reproduction of this type.

The following is a detailed description of my new impatiens cultivar based on plants produced under commercial practice in Cortez and Parrish, Fla. The description is based on plants grown outdoors in full sun during the fall, winter and spring months and under light shade during the summer months. Color references mare made to The Royal Horticultural Society Colour Chart except where general terms of ordinary dictionary significance are used.

Parentage:

Seedling No. 3-1 -96-63-1 from Seedling No. 3063-3-3 (from Impatiens Schlecterii P.I. 354260) × 3096-1 (from Impatiens Hawkerii P.I. 354251).

Propagation:

A. *Type cutting.*—Tip cuttings with 5 cm. stems.

B. *Time to initiate roots.*—10–14 days at 27° C. summer; 12–16 days at 18° C. winter.

C. *Rooting habit.*—Abundant.

Plant description:

A. *Form.*—Tall and upright, good branching habits.

B. *Habit of growth.*—Rate of growth moderate for this type of plant. Vegetative shoots are formed at the lower nodes and flowers at the higher nodes.

C. *Foliage description.*—Leaves are alternate with closely spaced nodes; leaves are simple. (1) Size: Average full grown leaf is 107 mm. long×35 mm. wide. Full grown leaves have petioles 30 mm. long. Young leaves have very short (3–5 mm.) petioles. (2) Shape: Elliptic, apex acute, base attenuate. (3) Texture: Smooth surface, glabrous. (4) Margin: Serrulate. (5) Color: Young foliage, top side between green 137B-C, under side close to green 138B; mature foliage, top side Green 137A, under side close to green 138B. (6) Venation: Pinnate, main vein infused with red.

Flowering description:

A. *Flowering habits.*—Very floriferous flowers occurring progressively at the base of each leaf petiole. Flowers are large and single.

B. *Natural flowering season.*—Flowering is indeterminate and occurs throughout the year except for periods of high light and high temperature in Florida.

C. *Flower buds.*—Conical, covered with 3 sepals. Upper two sepals are 11 mm. long×6 mm. wide, apex acuminate. Lower sepal is 15 mm. long×9 mm. wide, apex acuminate. Upper sepals are green in color and very slightly infused with a reddish pink color. Lower sepal colorless but infused with pink, with a green apex. A hollow spur (39 mm. long when full grown) is connected to lower sepal at the base. Spur is red in color.

D. *Flowers borne.*—On peduncles 63 mm. long; green in color.

E. *Quantity of flowers.*—One flower per leaf, occurring progressively at the base of each leave petiole.

F. *Petals.*—(1) Shape: Top petal heart-shaped with a broad rounded base. All other petals heart-shaped with pointed bases (2) Color: Top side red 45B when opening with slight lightening of color at the base of the bottom two petals, giving a slight indication of an eye; fading to close to red 52A; under side close to red 45D. (3) Number of petals: Five; with the middle and bottom petals slightly united at the base at each side. (4) Size of flowers: Top petal is 25 mm. long×36 mm. wide; 2 middle petals 30 mm. long×29 mm. wide; 2 lower petals 33 mm. long×33 mm. wide. Total flower diameter is 60 mm.

G. *Reproductive organs.*—(1) Stamens: Five in number, with lower stamen being shorter than the others. Stamens united in an asymmetrical tube surrounding. (a) Anther shape: Hooded, colorless heavily infused with red. (b) Pollen color: Cream. (2) Pistils: (a) Stigma shape: Five pointed star, colorless. (b) Style color: Cream, very short. (c) Ovaries: 5, celled, 5 mm., green.

Disease resistance:

No general diseases noted. Insect problems can include the two-spotted spider mite which can cause foliar injury and thrips which can cause stunting and injury to the growing tip.

I claim:

1. A new and distinct cultivar of impatiens plant named Vista Impatiens No. 10, as described and illustrated, and characterized by its vivid red and large flowers, dark green foliage, profuse blooming, and tall and upright habit, making it suitable for bedding plants and pot plant culture.

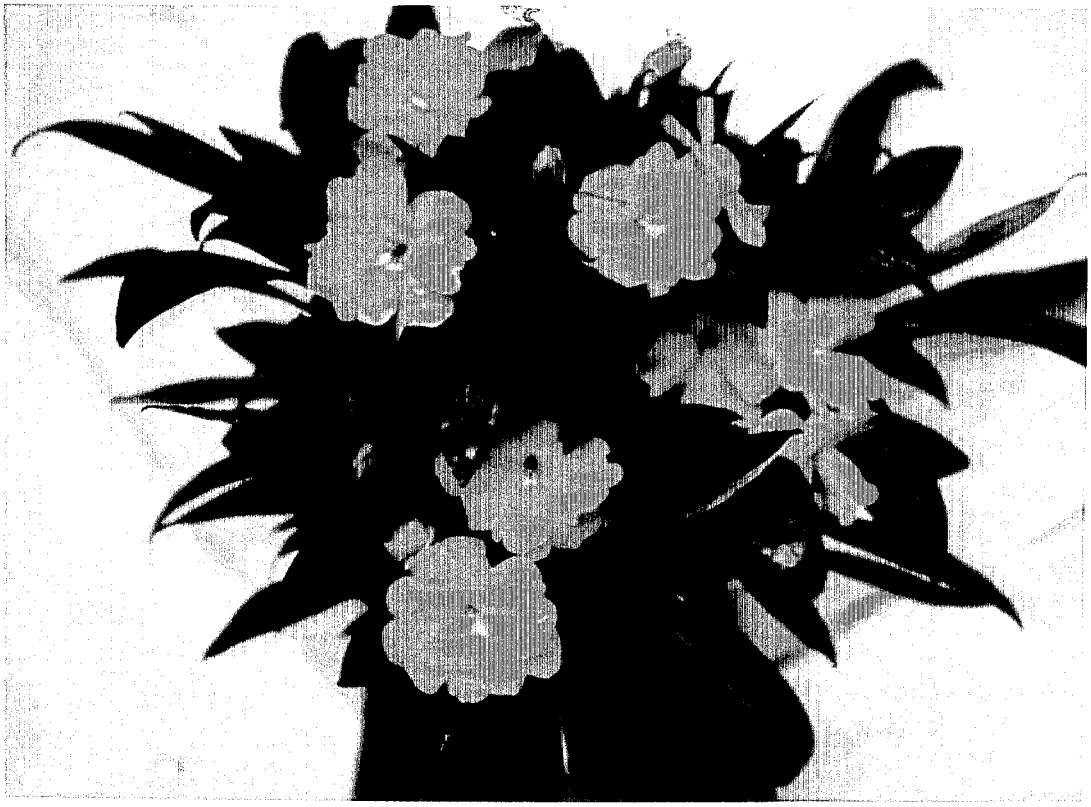

* * * * *